United States Patent [19]

Shander et al.

[11] Patent Number: 5,328,686
[45] Date of Patent: Jul. 12, 1994

[54] TREATMENT OF ACNE OR OF PSEUDOFOLLICULITIS BARBAE

[76] Inventors: Douglas Shander, 16112 Howard Landing Dr., Gaithersburg, Md. 20878; F. Eugene Harrington, 652 Fearrington Post, Fearrington Village, N.C. 27312; Mary C. Whitmore, 1 Vista Ave., Lynchburg, Va. 24503

[21] Appl. No.: 785,032

[22] Filed: Oct. 30, 1991

[51] Int. Cl.$^5$ .................... A61K 7/00; A61K 31/13
[52] U.S. Cl. ................................ 424/73; 514/844; 514/859; 514/887
[58] Field of Search ............... 424/73; 514/844, 859, 514/887

[56] References Cited

U.S. PATENT DOCUMENTS

| | | | |
|---|---|---|---|
| 4,139,638 | 2/1979 | Neri et al. | 424/324 |
| 4,161,540 | 7/1979 | Neri et al. | 424/324 |
| 4,191,755 | 3/1980 | Glen | 424/304 |
| 4,207,315 | 6/1980 | Voorhees et al. | 424/200 |
| 4,228,163 | 10/1980 | Bliss | 424/240 |
| 4,344,941 | 8/1982 | Wiechert et al. | 424/243 |
| 4,463,016 | 7/1984 | Burgess | 424/347 |
| 4,525,344 | 6/1985 | Tutsky | 424/73 |
| 4,720,489 | 1/1988 | Shander | 514/564 |
| 4,775,530 | 10/1988 | Perricone | 424/73 |
| 4,944,939 | 7/1990 | Moore | 424/73 |

FOREIGN PATENT DOCUMENTS 2840144 9/1978 Fed. Rep. of Germany.

OTHER PUBLICATIONS

Van Scott et al.; The Journal of Investigative Dermatology; pp. 405-428.
Rieger; Cosmetics and Toiletries; vol. 101; Dec. 1986; pp. 63-66.
Downing et al.; J. Am. Acad. Dermatol.; vol. 14; No. 2; Feb. 1986; pp. 221-222.
De Young; The Journal of Investigative Dermatology; vol. 82; No. 3; 1984; pp. 275-279.
Marsden et al.; Pharmacology of the Skin II; Chapter 35; pp. 473-481.
Mills et al.; Cosmetics & Toiletries; vol. 104; May 1989.
Plewig; The Journal of Investigative Dermatology; vol. 62; 1974; pp. 308-315.
Pegg et al.; The American Physiological Society; 1982; pp. C212-C221.
Tyms; The Physiology of Polyamines; vol. II; Chapter I; pp. 4-33.
Henry et al.; British Associate of Dermatologists; 1981; pp. 33-34.
Spencer; Cosmetics & Toiletries; vol. 100; Nov. 1985; pp. 47-49.
Dunn; AFP; vol. 39; No. 3; Sep. 1988; pp. 169-174.
Kligman et al.; Arch. Dermatol.; vol. 107; Apr. 1973; pp. 551-552.
Brown; Cutis; vol. 32; Oct. 1983; pp. 373-375.
Splinter et al.; Eur. J. Cancer and Clin. Oncology; vol. 22:1-E; 1985; pp. 61-67.
McCullough et al.; J. Investig. Dermatology; vol. 85; 1985; pp. 518-521.
McCullough et al.; J. Investig. Dermatology; vol. 81; 1983; pp. 388-392.
Kousa et al.; Acta Dermatovener (Stockholm); vol. 62; 1982; pp. 221-225.

Primary Examiner—Thurman K. Page
Assistant Examiner—James M. Spear
Attorney, Agent, or Firm—Fish & Richardson

[57] ABSTRACT

Patients suffering from acne and/or pseudofolliculitis barbae are treated by applying to the skin of the patient an inhibitor of ornithine decarboxylase.

4 Claims, No Drawings

TREATMENT OF ACNE OR OF PSEUDOFOLLICULITIS BARBAE

This invention relates to the treatment of acne and pseudofolliculitis barbae (PFB) by the topical application of compositions containing materials capable of inhibiting the action of the enzyme ornithine decarboxylase (ODC). In a preferred embodiment of this invention, such inhibitors are applied along with an antiandrogen or a retinoid.

BACKGROUND OF THE INVENTION

Although the exact mechanisms leading to acne are not known, antiandrogens, retinoic acid, steroids and antibiotics, inter alia have generally been proposed for its treatment, as described in U.S. Pat. Nos. 4,139,638; 4,161,540; 4,191,775; 4,344,943; and West German OLS no. 2,840,144.

PFB relates to the removal of hair by shaving or plucking. It has been treated by procedures such as the use of electric clippers or depilatories for hair removal, or by topical treatment with tretinoin (Retin-A), benzoyl peroxide, chlorohydroxyquinoline, chloroalkylphenols, phospholipids in combination with wheat germ oil and vitamin E, alpha-hydroxy acids, salicylic acid in combination with glucocorticoids and sulfur as shown for example in U.S. Pat. Nos. 4,228,163, 4,463,016; 4,525,344; 4,775,530; and 4,944,939; and in Klingman et al., Arch. Dermatol., vol. 107, 551–52 (1973).

Many of the treatments for PFB, and particularly for acne, produce such serious side effects that the treatment can be justified only in the most severe cases; other treatments are of limited effectiveness.

The compound 2-(difluoromethyl) ornithine (DFMO, 2-difluoromethyl-2.5-diaminopentanoic acid) and other inhibitors of ornithine dicarboxylase have been proposed for use in treating cancer and certain non-malignant diseases such as erythroderma, psoriasis, and some forms of dermatitis, etc. as described in Splinter et al., Eur. J. Cancer and Clin. Oncology, Vol. 22:1-E, 61–67 (1985); McCullough et al. J. Investig. Dermatology, Vol. 85, 518–521 (1985); McCullough et al., J. Investig. Dermatology, Vol. 81, 388–392 (1983); Kousa et al., Acta Dermatovener (Stockholm) Vol. 62, 221–224 (1982); and U.S. Pat. No. 4,207,315.

It has now been found that topical administration of a cytostatic nontoxic agent such as 2(difluoromethyl)-2.5-diaminopentanoic acid (d-difluoromethylornithine, DFMO) which inhibits the activity of the enzyme ornithine decarboxylase can be used to effectively ameliorate or control acne and/or PFB in patients with minimal or no unwanted side effects. DFMO can be used in combination with a topically active sebosuppressive agent such as an antiandrogen or a retinoid to gain the benefits of such agents for the treatment. Among the preferred inhibitors of ornithine decarboxylase, in addition to DFMO, which can be used in the present invention, are alpha-ethynyl ornithine; 6-heptyne-2,5-diamine; and esters of (E)-2-fluoromethyldehydroornithine. In choosing ODC inhibitors for use in the practice of the present invention it is important to avoid those having undesirable secondary pharmacological effects such as 5-hexyne-1,4-diamine. The inhibitors of ornithine decarboxylase are employed by dissolving or dispersing them in a conventional non-toxic pharmacologically acceptable vehicle or carrier which may be in the form of a lotion, cream, salve, ointment, or stick composition; while the precise concentration of inhibitor in vehicle or carrier is not critical it is generally desired that the composition contain from 1 to 20% of inhibitor by weight so that it can be applied to the affected areas of the skin of patients suffering from acne or PFB, particularly to the pimples or inflamed areas of the skin, at the rate of 40 to 800 micrograms per square centimeter. The composition is preferably applied only to the pustules, vacuoles or inflamed areas of the skin although application to adjacent areas need not be avoided.

Among the antiandrogens which can be used along with the ODC inhibitor are cyproterone acetate, chlormadinone acetate, 17-alpha-propyltestosterone, 17-alpha-allyitestosterone, $\alpha$-$\alpha$-$\alpha$-trifluoro-2-methyl-4'-nitro-m-propionotoluidide, 6$\alpha$-bromo-17$\beta$-hydroxy-17$\alpha$-methyl-4-oxa-5$\alpha$-androstane-3-one, 17$\beta$-acetoxy-4$\alpha$,5cyclo-A-homo-B-nor-5$\alpha$-androst-1-ene-3-one, and spironolactone. For minimal alterations of other androgen-mediated bodily functions through systemic action, 17-alpha-propyltestosterone or 17-alpha-allyltestosterone are preferred.

The following examples will serve to illustrate further the nature of the invention without acting as a limitation upon its scope.

EXAMPLE 1

Ten women suffering from mild to moderately severe grades of acne treated themselves twice daily over a 6 month period with an aqueous based vehicle (68% water, 16% ethanol, 5% propylene glycol, 5% dipropylene glycol, 4% benzoyl alcohol, and 2% propylene carbonate) containing 10g of DFMO per 100 ml of the total composition. Dermatological observations were recorded by a dermatologist who noted skin conditions prior to treatment, at 12 and 24 weeks of treatment, and 12 weeks after withdrawal of treatment.

Of the ten women on treatment nine showed significant improvement in their acne condition. Of the nine who responded, four demonstrated complete resolution of acne within 12 weeks, and a fifth subject, for whom no 12 week observation was available, exhibited complete clearance by the 24th week. The four subjects in which acne was not completely cleared demonstrated progressively marked improvements through the course of treatment. After cessation of treatment at twelve weeks, continued observations were made on the nine of the original 10 subjects including the eight who responded to treatment. This post treatment follow up revealed that seven of eight exhibited a recurrence of acne after withdrawal of treatment. The total clearance or marked improvement in acne in 9 of 10 subjects after treatment with elfluornithine and its recurrence after treatment cessation demonstrates the efficacy of DFMO.

EXAMPLE 2

Nine women suffering from pseudofolliculitis treated themselves and were evaluated as described in Example 1. Five exhibited complete clearance, four of whom cleared within 12 weeks. Four additional women showed progressive improvements during 24 weeks of treatment. Of the nine women with pseudofoliculitis six were women from the group of 10 in Example 1 who suffered from acne as well. In the six women with both acne and PFB, three demonstrated complete clearing of both conditions and the other three exhibited substantial clearing of both conditions.

What is claimed is:

1. The process of treating acne in a patient, which comprises applying to an affected area of skin of a patient suffering from acne a composition comprising a non-toxic pharmacologically acceptable vehicle and an inhibitor of the enzyme ornithine decarboxylase in an amount effective to treat acne.

2. The process as claimed in claim 1 in which said inhibitor is 2-(difluoromethyl)-2,5-diaminopentanoic acid.

3. The process of treating pseudofolliculitis barbae in a patient, which comprises applying to an affected area of skin of a patient suffering from pseudofolliculitis barbae a composition comprising a non-toxic pharmacologically acceptable vehicle and an inhibitor of the enzyme ornithine decarboxylase in an amount effective to treat pseudofolliculitis barbae.

4. The process as claimed in claim 3 in which said inhibitor is 2-(difluoromethyl)-2,5-diaminopentanoic acid.

* * * * *